United States Patent [19]
Walser

[11] Patent Number: 5,591,736
[45] Date of Patent: Jan. 7, 1997

[54] METHOD OF RETARDING THE PROGRESSION OF CHRONIC RENAL FAILURE

[75] Inventor: Mackenzie Walser, Ruxton, Md.

[73] Assignee: The Johns Hopkins University, Baltimore, Md.

[21] Appl. No.: 497,958

[22] Filed: Jul. 3, 1995

[51] Int. Cl.$^6$ ................................................. A61K 31/56
[52] U.S. Cl. ............................................................ 514/178
[58] Field of Search ............................................. 514/178

[56] References Cited

U.S. PATENT DOCUMENTS

| | | | |
|---|---|---|---|
| 4,100,160 | 7/1978 | Walser | 424/274 |
| 4,228,099 | 10/1980 | Walser | 260/501.11 |
| 4,352,814 | 10/1982 | Walser | 424/273 R |
| 4,496,556 | 1/1985 | Orentreich | 514/178 |
| 4,542,129 | 9/1985 | Orentreich | 514/178 |
| 4,752,619 | 6/1988 | Walser et al. | 514/564 |
| 5,175,144 | 12/1992 | Walser | 514/2 |

OTHER PUBLICATIONS

Abstract (Accession Number QD586–0004) of Araneo et al., "Dehydropepiandrosterone Functions as More than an Antiglucocorticoid in Preserving Immunocompetence after Thermal Injury" *Endocrinology* 136(2): 393–401 (Feb. 1995).

Kalimi et al., "Anti–Glucocorticoid Effects of Dehydroepiandrosterone (DHEA)", *Mol. Cell. Biochem.* 131:99–104 (1994).

Lucas et al., "Prevention of Autoantibody Formation and Prolonged Survival in New Zealand Black/New Zealand White $F_1$ Mice Fed Dehydroisoandrosterone", *J. Clin. Invest.* 75:2091–2093 (1995).

McIntosh et al., "Strain Differences in the Dose–Response Curves of Adrenalectomized, Starved–Refed Rats to Dehydroepiandrosterone (DHEA) (42657)", *Proc. Soc. Exp. Biol. Med.* 187:216–222 (1988).

Meikle et al., "The Presence of a Dehydroepiandrosterone–Specific Receptor Binding Complex in Murine T Cells", *J. Steroid Biochem. Molec. Biol.* 42(3/4):293–304 (1992).

Meikle et al., "Adrenal Androgen Secretion and Biologic Effects", *Endrocinol. Metab. Clinics N. Amer.* 20(2):381–400 (1991).

Pashko et al., "Inhibition of Proteinuria Development in Aging Sprague–Dawley Rats and C57BL/6 Mice by Long–Term Treatment with Dehydroepiandrosterone", *J. Gerontol.* 41(4):433–438 (1986).

Suzuki et al., "Dehydroepiandrosterone Enhances IL2 Production and Cytotoxic Effector Function of Human T Cells", *Clin. Immunol. Immunopath.* 61:202–211 (1991).

Svec et al., "The Effect of DHEA Given Chronically to Zucker Rats (43883)", *Proc. Soc. Exp. Biol. Med.* 209:92–97 (1995).

van Vollenhoven et al., "An Open Study of Dehydroepiandrosterone in Systemic Lupus Erythematosus", *Arthritis Rheum.* 37(9): 1305–1310 (1994).

Walser et al., "Progression of Chronic Renal Failure is Related to Glucocorticoid Production", *Kidney Int.* 34:859–866 (1988).

Walser et al., "Progression of Chronic Renal Failure in Patients Given Ketoacids Following Amino Acids", *Kidney Int.* 32:123–128 (1987).

Winer et al., "Preservation of Normal Adrenal Androgen Secretion in End Stage Renal Disease", *Metabolism* 31(3):269–273 (1982).

Zumoff et al., "Subnormal Plasma Adrenal Androgen Levels in Men with Uremia", *J. Clin. Endocrin. Metab.* 51(4):801–805 (1980).

*Primary Examiner*—Raymond Henley, III
*Attorney, Agent, or Firm*—Panitch, Schwarze, Jacobs & Nadel, P.C.

[57] ABSTRACT

The progression of chronic renal failure in humans may be retarded by administration of dehydroepiandrosterone (DHEA) in effective amounts. The administration of DHEA is preferably oral at a dose of about 400 to 1600 mg/day. Patients suffering from severe chronic renal failure are also preferably maintained on a protein-restricted diet during DHEA administration.

12 Claims, No Drawings

METHOD OF RETARDING THE PROGRESSION OF CHRONIC RENAL FAILURE

FIELD OF THE INVENTION

The present invention relates to a treatment method for retarding the progression of chronic renal failure in humans.

BACKGROUND OF THE INVENTION

Advanced chronic renal disease in humans is typically associated with multiple endocrine and metabolic abnormalities. Conventional therapy for treating chronic renal failure has focused on protein-restricted diets in conjunction with administration of ketoacid analogs of amino acids; see U.S. Pat. Nos. 4,100,160, 4,228,099 and 4,352,814, all of Walser, and U.S. Pat. No. 4,752,619 of Walser et al.

Another technique for slowing the progression of chronic renal failure is described by Walser in U.S. Pat. No. 5,175,144 and in U.S. application Ser. No. 07/996,757, where the treatment involves administration of ketoconazole or other agent that suppresses glucocorticoid production.

Although these therapies may be useful in slowing the progression of chronic renal failure in many patients, the mechanism and factors that lead to chronic renal failure are still not well understood.

The human adrenal cortex secretes a variety of steroid hormones, including androgens, glucocorticoids and mineralocorticoids. The predominant androgen produced by the adrenal cortex is dehydroepiandrosterone (DHEA). DHEA is a nineteen carbon atom steroid hormone that is well known to serve as the precursor of sex hormones such as testosterone, dihydrotestosterone, estradiol and estrone.

In recent years, many studies have been undertaken to elucidate the biological role of DHEA. The results of this research are far from conclusive but suggest that DHEA has many diverse biological, biochemical and physiological effects involving various cell types, tissues and organs.

A review article by Meikle et al. in "Adrenal Androgen Secretion and Biologic Effects," Endrocrinol. Metab. Clinics N. Amer., 20:381–400 (1991), describes some of the biologic effects of DHEA and underscores the fact that its normal functions are not well understood.

DHEA studies involving laboratory rats or mice have reported that administration of DHEA prevents obesity, inhibits tumor development, ameliorates diabetes, prevents autoimmune anemia, prevents double-stranded DNA antibody formation and prolongs survival in lupus erythematosus-susceptible mice (see for example, Meikle et al. (supra); Lucas et al., J. Clin. Invest., 75:2091–2093 (1985); and Svec et al., Proc. Soc. Exp. Med. Biol., 209:92–97 (1995)).

A recent study in humans by van Vollenhoven et al., "An Open Study of Dehydroepiandrosterone in Systemic Lupus Erythematosus," Arthritis Rheum., 37:1305–1310 (1994), confirmed early animal studies that DHEA was useful in treating mild to moderate systemic lupus erythematosus. Three of the ten patients in the study also had proteinuria, which was improved by the administration of DHEA.

The Meikle et al. review article (supra) likewise mentions, in its discussion under renal effects, that aging laboratory rats, which typically develop proteinuria, had this condition reduced by long term treatment with DHEA.

Studies of patients with chronic renal failure have reported that plasma levels of the adrenal androgen DHEA in such patients are low (see Zumoff et al., "Subnormal Plasma Adrenal Androgen Levels in Men With Uremia," J. Clin. Endocrinol. Metab., 51:801–805 (1980)) but that the adrenal gland secretory capacity for production of DHEA and of other adrenal androgens and steroids is undiminished, as demonstrated by stimulation with a known adrenal stimulus, cosyntropin (see Winer et al., "Preservation of Normal Adrenal Androgen Secretion in End Stage Renal Disease," Metabolism, 31:269–273 (1982)).

Meikle et al. (supra) report that studies have shown that DHEA levels in the body are significantly reduced by the administration of a synthetic glucocorticoid. A recent study of the biologic effects of DHEA identified an anti-glucocorticoid effect of DHEA but concluded that minimal information was available on the cellular and molecular mechanism of DHEA; see Kalimi et al., "Anti-glucocorticoid Effects of Dehydroepiandrosterone (DHEA)", Mol. Cell. Biochem., 131:99–104 (1994).

One reported medical use for DHEA is as a topical treatment for preventing dry skin, described in U.S. Pat. Nos. 4,496,556 and 4,542,129 of Orentreich. The former patent notes that oral ingestion of DHEA results in the undesirable increase in oil production by all sebaceous glands over the entire body.

These reports in the prior art fail to suggest any usefulness of DHEA in the context of a treatment method for retarding the progression of chronic renal failure.

SUMMARY OF THE INVENTION

According to the present invention, it has now been discovered that the progression of chronic renal failure in human beings may be retarded by administering to a human suffering from chronic renal failure an effective amount of dehydroepiandrosterone (DHEA).

The DHEA is preferably administered orally and in a dose amount of about 400 to about 1600 mg DHEA per day.

DETAILED DESCRIPTION OF THE PREFERRED EMBODIMENTS

Dehydroepiandrosterone (DHEA) is a well known naturally-occurring androgenic steroid having the structural formula:

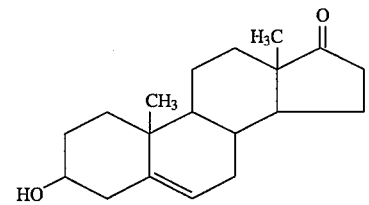

DHEA is 3-hydroxyandrost-5-en-17-one and is also designated in the literature by any of several synonyms, e.g., dehydroisoandrosterone, prasterone.

DHEA may be isolated and/or synthesized by known methods; see Merck Index, 11th ed. (1989) page 1221, Ref. 7710 Prasterone. DHEA is also manufactured by various commercial suppliers and is generally available in commerce.

DHEA and its sulfated form DHEA-S are secreted by the human adrenal cortex and circulate in the bloodstream.

References in this disclosure to DHEA are intended to include DHEA per se as well as the sulfated form, DHEA-S, since plasma DHEA-S has a relatively long half life as compared with plasma DHEA. Other derivatives of DHEA that provide equivalent functionality in retarding chronic renal failure progression are also intended to be within the scope of this invention.

Administration of DHEA in the method of this invention is preferably by oral ingestion, most preferably in an oral dosage form such as tablets or capsules. The dosage rate should be in the range of about 400 to about 1600 mg DHEA per day, for adult human beings, preferably as two daily doses.

Although not necessary in this invention, a protein-restricted diet may be desirable for reducing symptoms in patients severely affected with chronic renal failure. In such cases, the level of dietary protein is preferably restricted to less than 0.6 gram protein per day per kilogram of ideal body weight.

The method of this invention is generally useful for treating chronic renal failure. In particular, the treatment may be used where chronic renal failure results from polycystic kidney disease, from chronic glomerulonephritis, from diabetes, from interstitial nephritis, and/or from hypertension.

In order to discover factors predictive of the raze of progression of chronic renal failure, a clinical study was carried out under the inventor's supervision on a large group of patients, with many types of chronic renal disease being represented. The study monitored various factors that the inventor believed might be implicated in or predictive of the progression of chronic renal failure.

Clinical Study Methods

Seventy-six patients with chronic renal failure, not yet on dialysis, were studied. Of these patients, 45 were males and 31 were females. Their average age was 49, with ages ranging from 23 to 79 years. Diagnoses of chronic renal failure in these patients were as follows: chronic glomerulonephritis 17; diabetic nephropathy 15; hypertensive nephrosclerosis 15; polycystic kidney disease 9; interstitial nephritis 7; other disorders 13.

The clinical study monitored various factors that were suspected of being implicated in the progression of chronic renal failure. These factors included age, gender (male/female), presence or absence of polycystic kidney disease. Other factors, measured as substances present in the 24-hour excreted urine, included 24-hour urinary protein excretion; 24-hour urinary excretion of 17-hydroxycorticosteroid (a measure of glucocorticoid production, the primary constituent being cortisol); and 24-hour urinary excretion of nitrate (a measure of the rate or production of nitric oxide).

Progression rate of chronic renal failure in the study group was determined by measurements of glomerular filtration rate, falling glomerular filtration rates being indicative of more rapid chronic renal failure progression.

Glomerular filtration rate at entry into the study averaged 25 ml per minute (normal =125 ml per minute), with a range of 5 to 83 ml per minute. Glomerular filtration rate was measured by the Nuclear Medicine Laboratory of Johns Hopkins Hospital as the urinary clearance of $^{99m}$technetium-labelled diethylenetriamine acetic acid, averaged over three collection periods, during water loading. In order to quantitate rate of progression of chronic renal failure, glomerular filtration rate was measured an average of 8 times per patient during a follow-up period averaging 13 months per patient.

Other aspects of treatment, such as diet, were held constant. At each visit, a 24-hour urine collection was obtained and blood was drawn; serum or plasma was stored in the frozen state, as was an aliquot of 24-hour urine.

DHEA-S in serum (or plasma) was measured by radioimmunoassay. 17-hydroxycorticosteroids in urine were measured by the Porter-Silber reaction. Urinary nitrate was measured by the Griess reaction after converting nitrate to nitrite by means of nitrate reductase. Urinary protein was measured by the Johns Hopkins Hospital Chemistry Laboratory.

Progression rate was calculated as the linear regression slope of glomerular filtration rate on time. This rate and its variance were then entered into a multiple regression program, using progression rate as the dependent variable and as independent variables serum DHEA-S, 24-hour urinary protein, urinary 17-hydroxycorticosteroids, urinary nitrate, age, gender and presence or absence of polycystic kidney disease. The analysis was weighted by the reciprocal of the variance of the slope of progression rate. Calculations were performed on an IBM Mainframe computer using a statistical program called PROC REG, which is part of a software package known as SAS (SAS/Stat Users Guide, Version 6, Chapter 36, SAS Institute, Cary, N.C. 27511-8000).

Clinical Study Results

Several regression analyses were carried out, using data generated in the clinical study. In the multiple regression analyses, weighted analysis was used in which the weights were the reciprocal of the variances of the glomerular filtration rate over time. This procedure served to give greater weight to those progression rates that were measured more reliably and lower weight to those measured less reliably. The regression analysis served to determine whether a correlation existed between the progression rate of chronic renal failure (the dependent variable) and one or more of the factors monitored during the study (the independent variables).

The first analysis indicated that measurements of DHEA-S plasma or serum levels were not a significant predictor (data not shown) of the progression rate of chronic renal failure. The ratio of 17-hydroxycorticosteroid 24-hour excretion ("glucocorticoid production") to plasma DHEA-S level, on the other hand, was a significant predictor, as shown by the regression analysis results in Table 1 (p=0.0063, where p indicates the probability of this correlation arising by chance). This variable is inversely related to chronic renal failure progression, as indicated by the negative constant. Thus, patients who have high ratios of glucocorticoid production to plasma DHEA-S will exhibit more rapid chronic renal failure progression (i.e., the glomerular filtration rate falls more rapidly). Conversely, increasing the plasma DHEA level, e.g., by administering DHEA, will reduce the above-noted ratio, leading to a reduction in the chronic renal failure progression.

The second regression analysis was a multiple variable analysis that included several factors as independent variables:

plasma DHEA-S level 17-hydroxycorticosteroid 24-hour excretion protein 24-hour excretion presence or absence of polycystic kidney disease gender age The last two independent variables, gender and age, were included to take into account the known dependence of plasma DHEA levels on these two factors. Plasma levels of DHEA, in the DHEA-S form, are lower in women than in men and have been shown to reach a peak in early adult life and then decline with advancing age.

The results of this second regression analysis are summarized in Table 2 and show that plasma DHEA-S itself is highly predictive of chronic renal failure progression (p=0.0054). The correlation is positive, with an increase in plasma DHEA-S correlating with a reduced progression rate of chronic renal failure, i.e., glomerular filtration rate increases with increasing plasma DHEA-S levels.

The regression analysis data in Table 2 also show that glucocorticoid production (17-hydroxycorticosteroid 24-hour excretion), protein 24-hour excretion and the presence/absence of polycystic kidney disease are highly predictive, in an inverse relationship, with chronic renal failure progression. As each of these factors increases, the glomerular filtration rate falls more rapidly.

The two remaining independent variables, gender and age, showed no significant correlation with chronic renal failure progression rate.

The third regression analysis was similar to the previous multiple regression analysis, except that one more factor was included as an additional dependent variable: nitrate 24-hour excretion. The results of this third regression analysis are summarized in Table 3.

The data show that the correlation of plasma DHEA-S levels with chronic renal failure progression is essentially the same as that obtained in the second regression analysis. Plasma DHEA-S is highly predictive of chronic renal failure progression (p=0.0095), as described for the previous regression analysis.

The newly added dependent variable, nitrate 24-hour excretion, is shown in this analysis to be highly predictive, in an inverse relationship, to chronic renal failure progression, i.e., increased nitrate excretion correlates with more rapidly falling glomerular filtration rates.

This third regression analysis also indicates that glucocorticoid production is no longer predictive (contrary to the good correlation indicated for this independent variable in the second regression analysis) of chronic renal failure progression.

With respect to the other remaining independent variables, the results in this third multiple regression analysis are similar to the correlations established in the previous multiple regression analysis.

In summary, the regression analyses of the clinical study data demonstrate that plasma or serum levels of DHEA-S are highly predictive of the progression of chronic renal failure and that increased plasma DHEA-S levels correlate well with the slowing or retardation of chronic renal failure.

These findings are a basis for the method of the present invention, in which the progression of chronic renal failure is retarded by the administration of DHEA to patients suffering from chronic renal failure.

While the inventor does not wish to be bound by any particular theory for explaining the efficacy of DHEA in this invention, several observations can be made that indicate a complex role for DHEA.

The data obtained in the above-noted clinical study show that plasma levels of DHEA-S are a significant predictor of chronic renal failure progression. By contrast, the results of the third regression analysis indicate that levels of glucocorticoid production (as measured by levels of urinary 17-hydroxycorticosteroid, cortisol being the predominant glucocorticoid) is not by itself a good predictor of chronic renal failure progression. The absence of a correlation is strong evidence that the method of this invention cannot be explained by DHEA-S serving merely as an anti-glucocorticoid, since control of cortisol production would in that case be expected to be highly predictive of progression of chronic renal failure.

The diversity of biologic effects attributable to DHEA, as evidenced by numerous studies reported in the prior art, include studies that find no evidence of DHEA binding to glucocorticoid receptor cells (and thus blocking glucocorticoids) and no evidence of DHEA blocking enzymatic steps in the synthesis of cortisol, the principal glucocorticoid in humans.

Consequently, the theory and mechanism behind the treatment method of the present invention is not understood and cannot be explained by references to prior art teachings concerning the biologic effects of DHEA.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

TABLE 1

Summary of Regression Analysis
Correlation of (Glucocorticoid Production To Plasma DHEA-S) Ratio to Chronic Renal Failure Progression (Glomerular Filtration Rate)

| | |
|---|---|
| Number of Patients | 76 |
| F Value | 7.904 |
| $R^2 =$ | 0.0965 |
| b = | −32.720 |
| T Statistic = | −2.811 |
| P = | 0.0063 |

TABLE 2

Summary of Multiple Regression Analysis
Correlation of Six Independent Variables To Chronic Renal Failure Progression (Glomerular Filtration Rate)

| | | | |
|---|---|---|---|
| Number of Patients | | 76 | |
| F Value | | 9.122 | |

| Independent Variable | b | P | T Statistic |
|---|---|---|---|
| X1 | 0.0000607 | 0.0054 | 2.870 |
| X2 | −0.0737 | 0.0001 | −4.583 |
| X3 | −0.0734 | 0.0003 | −3.815 |
| X4 | −0.312 | 0.0031 | −3.063 |
| X5 | −0.0384 | 0.4776 | −0.714 |
| X6 | 0.00119 | 0.5315 | 0.629 |

Where:
X1 = plasma DHEA-S level
X2 = 17-hydroxycorticosteroid 24-hour excretion
X3 = protein 24-hour excretion
X4 = presence or absence of polycystic kidney disease
X5 = gender
X6 = age

TABLE 3

Summary of Multiple Regression Analysis
Correlation of Seven Independent Variables To Chronic Renal Failure Progression (Glomerular Filtration Rate)

| | | | |
|---|---|---|---|
| Number of Patients | | 71 | |
| F Value | | 9.985 | |

| Independent Variable | b | P | T Statistic |
|---|---|---|---|
| X1 | 0.0000594 | 0.0095 | 2.675 |
| X2 | −0.0369 | 0.1104 | −1.619 |
| X3 | −0.0832 | 0.0002 | −3.971 |
| X4 | −0.308 | 0.0041 | −2.982 |
| X5 | 0.0346 | 0.6340 | 0.478 |

TABLE 3-continued

Summary of Multiple Regression Analysis
Correlation of Seven Independent Variables To Chronic Renal
Failure Progression (Glomerular Filtration Rate)

| X6 | 0.0000390  | 0.9857 | 0.018  |
| X7 | −0.000311 | 0.0012 | −3.404 |

X1 = plasma DHEA-S level
X2 = 17-hydroxycorticosteroid 24-hour excretion
X3 = protein 24-hour excretion
X4 = presence or absence of polycystic kidney disease
X5 = gender
X6 = age
X7 = nitrate 24-hour excretion

I claim:

1. A method of retarding the progression of chronic renal failure in human beings comprising administering to a human suffering from chronic renal failure an effective amount of dehydroepiandrosterone (DHEA).

2. The method of claim 1 wherein the DHEA is administered orally.

3. The method of claim 2 wherein the DHEA is administered in a dose amount of about 400 to about 1600 mg/day.

4. The method of claim 2 wherein the DHEA is administered in the form of a tablet or capsule.

5. The method of claim 1 wherein the DHEA is administered to a human while said human is on a protein-restricted diet.

6. The method of claim 5 wherein the protein is restricted to less than about 0.6 g. protein per day per kilogram of ideal body weight.

7. The method of claim 1 wherein the DHEA is selected from the group consisting of DHEA and DHEA-S.

8. The method of claim 1 wherein the chronic renal failure results from polycystic kidney disease.

9. The method of claim 1 wherein the chronic renal failure results from chronic glomerulonephritis.

10. The method of claim 1 wherein the chronic renal failure results from type I diabetes.

11. The method of claim 1 wherein the chronic renal failure results from interstitial nephritis.

12. The method of claim 1 wherein the chronic renal failure results from hypertension.

* * * * *